United States Patent [19]
Guillen

[11] Patent Number: 6,074,673
[45] Date of Patent: Jun. 13, 2000

[54] SLOW-RELEASE, SELF-ABSORBING, DRUG DELIVERY SYSTEM

[76] Inventor: Manuel Guillen, 8303 Arlington Blvd. #201, Fairfax, Va. 22031

[21] Appl. No.: 08/639,101

[22] Filed: Apr. 22, 1996

[51] Int. Cl.[7] .............................. A61K 9/50; B01J 13/02; B32B 5/16

[52] U.S. Cl. ...................... 424/501; 424/502; 264/4.32; 264/4.33; 428/402.21

[58] Field of Search .................................. 424/501, 502; 264/4.32, 4.33; 428/402.21

[56] References Cited

U.S. PATENT DOCUMENTS

| | | | |
|---|---|---|---|
| 2,683,136 | 7/1954 | Higgins ................................. | 260/78.3 |
| 3,297,033 | 1/1967 | Schmitt et al. ....................... | 128/335.5 |
| 3,435,008 | 3/1969 | Schmitt et al. ....................... | 260/78.3 |
| 3,442,871 | 5/1969 | Schmitt et al. ....................... | 260/78.37 |
| 3,457,280 | 7/1969 | Schmitt et al. ....................... | 260/340.2 |
| 3,468,853 | 9/1969 | Schmitt et al. ....................... | 260/78.3 |
| 3,597,450 | 8/1971 | Schmitt et al. ....................... | 260/340.2 |
| 4,122,129 | 10/1978 | Casey et al. .......................... | 260/860 |
| 5,019,094 | 5/1991 | Bezwada et al. ...................... | 606/230 |
| 5,403,347 | 4/1995 | Roby et al. ............................ | 606/230 |

OTHER PUBLICATIONS

Mason, WW, "Preparation of Antigents for the Diagnosis and Treatment of Allergy. Part 1: Raw Materials", Ear, Nose, & Throat Journal.74(1):14–5, Jan. 1995.

Rumbyrt, JS and Borish, LC, "Home Administration of Allergen Extracts", JAMA, 273(11):897, Mar. 15, 1995.

Frewm AJ., Conventional and Alternative Allergen Immunotherapy: Do They Work? Are They Safe? Clinical & Experimental Allergy, 24(5):416–22, May 1994.

Grammar, L and Shaughnessy, MA, "Allergen Immunotherapy: Definition, Indication, and Reactions", Allergy Proceedings, 14(2):108–9, Mar.–Apr. 1993.

G. Ertan, et al., "Release Characteristics of Implantable Cylindrical Polyethlene Matrices", J. Pharm. Pharmacol., pp. 229–235, 1997.

A. Dash et al., "An Implantable Dosage Form for the Treatment of Bone Infection", Pharmaceutical Research, vol. 9, No. 8, pp.993–1002, 1992.

J. Golenser et al., "The Treatment of Animal Models of Malaria with Iron Chelators by use of a Novel Polymeric Device for Slow Drug Release", J. Pharmacol Exp Ther, vol. 281, No. 3, pp. 1127–1135, 1997.

B. Jeong et al., "Biodegradable Block Copolymers as Injectable Drug–Delivery Systems", Nature, vol. 388, pp.860–862, Aug. 28, 1997.

Gangadharam et al., "Experimental Chemotherapy of Tuberculosis Using Single Dose Treatment With Isoniazid in Biodegradable Polymers", Journal of Antimicrobial Chemotherapy, 33, pp.265–271, 1994.

C. Krewson et al., "Stabilization of Nerve Growth Factor in Controlled Release Polymers and in Tissue", J. Biomater. Sci. Polymer Edn., vol. 8, No. 2, pp. 103–117 (1996).

M. Kurisawa et al., "Recent Trends in Drug Delivery Systems Using Biomaterials", Nippon Rinsho, vol. 54, pp. 2004–2011, 1996.

(List continued on next page.)

*Primary Examiner*—Carlos A. Azpuru
*Attorney, Agent, or Firm*—Klima & Pezzlo P.C.

[57] ABSTRACT

The present invention is directed to an implantable, slow-release, self-absorbing, biologically compatible drug delivery system such as slow-release pharmaceutical compositions, including for example, slow-release, allergy desensitization compositions containing one or more allergens in combination with a biologically-compatible, self-absorbing matrix. The present system is useful for treating disorders including, for example, infections, deficiencies or allergies. The present invention is also directed to methods of treating a patient suffering from a disorder, as well as methods for desensitizing a patient to one or more allergens. The present invention also relates to a device for implanting the present composition in a patient.

12 Claims, 1 Drawing Sheet

OTHER PUBLICATIONS

R. Duncan, "Drug–Polymer Conjugates: Potential for Improved Chemotherapy", Anti–Cancer Drugs, vol. 3, pp. 175–210, 1992.

Hashizoe et al., "Biodegradable Polymeric Device for Sustained Intravitreal Release of Ganciclovir in Rabbits", Current Eye Research, vol. 16, pp.633–639, 1997.

Menei et al., "Drug Targeting into the Central Nervous Systems by Sterotactic Implantation f Biodegradable Microspheres", vol. 34, No. 6, June 1994.

Brem et al., "Placebo–Controlled Trail of Safety and Efficacy of Intraoperative. . .", Lancet, 345, pp.1008–1012, 1995.

Hashizoe et al., "Implantable Biodegradable Polymeric Device in the Treatment of. . .", Current Eye Research, vol. 14, pp. 473–477, 1995.

Brem et al., "Biodegradable Polymers for Controlled Delivery of Chemotherapy. . .", J. Neurosurg. 80, pp.283–290, 1994.

U. Kohler et al., "A New Animal Model of Dopamine Supersensitive Using S.C. implatation of Haloperidol Releasing Polymer", Neuroscience Letters, 170, pp. 99–102, 1994.

Shikani et al., "Polymer Delivery of Chemotherapy for Squamous Cell Carcinoma of the Head and Neck", Arch Otolaryngol Head Neck Surg, vol. 120, pp.1242–1247, 1994.

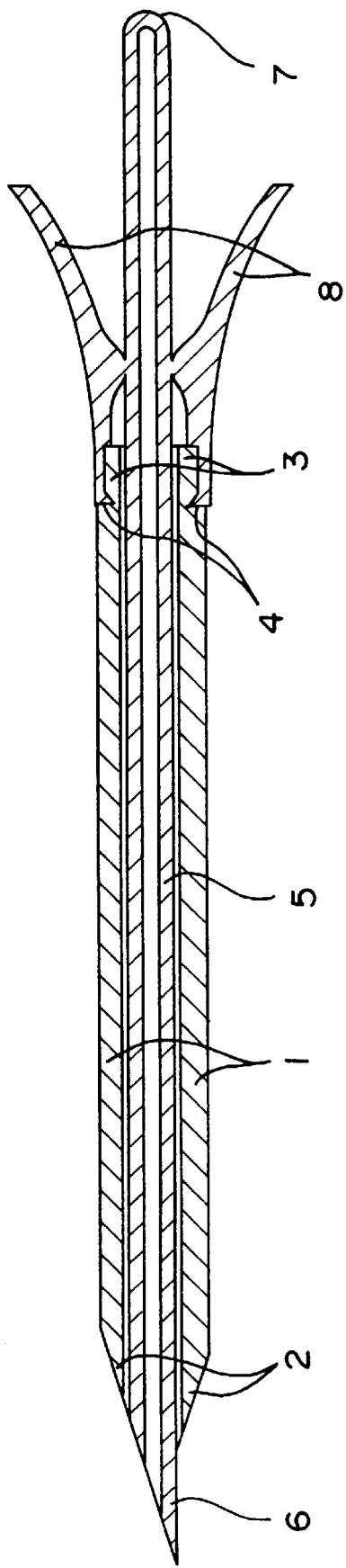
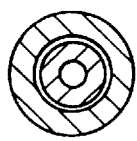

SLOW-RELEASE, SELF-ABSORBING, DRUG DELIVERY SYSTEM

FIELD OF THE INVENTION

The present invention relates to an implantable, slow-release, self-absorbing, biologically-compatible, drug delivery system including slow-release pharmaceutical compositions, methods of administering such compositions and methods of treating disorders with such compositions. More particularly, the present invention relates to a slow-release, self-absorbing, allergy desensitization system including slow-release allergy desensitization compositions and methods of desensitizing a patient using such compositions, as well as a device for implanting the composition at a site in a patient.

BACKGROUND OF THE INVENTION

Traditionally, medications have been administered by various routes including orally, subcutaneously, intramuscularly, or intravenously. Other drug delivery systems include, for example, transdermal patches, membrane encased cells genetically engineered to secrete a desired drug, for example, nerve growth factor or insulin, and slow-release drug systems including for example, NORPLANT.

Traditional routes of administration are problematic in that they require strict patient compliance, i.e., when medication is administered orally, such as an antibiotic, hormone, vitamin, or when repeated visits to the doctor are necessary because the route of administration is by injection. These methods of administration are especially problematic in cases where the patient is a child, is elderly, or where the medication must be administered on a chronic basis, i.e., weekly allergy injections. Compliance with taking medication is a problem for many adults, i.e., they simply forget to take it. Further, weekly allergy injections deter many people from obtaining needed treatment because weekly injections at the doctor's office interferes with their activities or schedules.

Transdermal patches are currently used to administer drugs such as hormones, estrogen, nicotine (NICORETTE to stop smoking), and nitroglycerin (for angina pain). While this system is quite good, a drug must be able to penetrate the skin barrier in order to be administered via a transdermal patch. Many drugs cannot be administered in effective amounts transdermally. Other slow-release delivery systems such as NORPLANT are useful, but they require the removal of the matrix itself after the drug has been completely absorbed over time. Thus, surgery is required to insert the composition and to remove the exhausted matrix from the patient.

The present invention solves the problems presented by the prior art routes, forms and methods of administration by providing an implantable pharmaceutical composition containing the active substance in a biologically-compatible, self-absorbing matrix. Further, the present invention provides an implantation device for implanting the present pharmaceutical composition in the subcutaneous tissue of a patient at a desired site.

SUMMARY OF THE INVENTION

The present invention is directed to a slow-release, self-absorbing, pharmaceutical composition containing one or more active agents in combination with a biologically-compatible, self-absorbing matrix. More particularly, the present invention is directed to a slow-release, self-absorbing allergy desensitization composition containing one or more allergens in combination with a biologically-compatible, self-absorbing matrix. An objective of the present invention is to remove any dosage error due to patient non-compliance as well as minimize the amount of time a patient needs to spend in a doctor's office. Traditionally, allergy desensitization injections have had to be administered to a patient weekly by a doctor. This causes a major inconvenience for most people with significant allergic symptoms such as allergic rhinitis (hay fever), seasonal allergic rhinitis due to, for example, pollens, and asthma due to allergens.

The present composition, methods and device allow such patients to receive the same active ingredients in a slow-release, self-absorbing form at intervals of from about two weeks to about two months preferably at intervals of about one month, depending on the rate of absorption of the matrix in the subcutaneous tissue of the patient, and the degree of sensitivity of the patient. Once initial desensitization is reached maintenance dosage units can be implanted at intervals of about two to six months, preferably at intervals of about four months and most preferably at intervals of about every six months. Since the present composition contains a self-absorbing matrix, no removal of the matrix is necessary after the complete absorption of the active agent by the patient. After the initial desensitization series, patients need only receive a maintenance amount of the present allergy desensitization composition at intervals of from approximately two to ten months, preferably every four to eight months, and most preferably every six months, again depending on the rate of absorption of the matrix in the patient and the degree of sensitivity of the patient to the allergen(s).

The degree of sensitivity of a patient is easily determined by a medical doctor based on the patients' clinical history and allergy test results, either allergy skin tests or allergy laboratory tests, such as a RAST test. The RAST test is a radioallergosorbent test by which allergen-specific IgE antibodies are detected in the serum of a patient (*Allergy, Principles & Practice,* Middleton, Reed, Ellis, Adkinson, Yunginger, 3rd Edition, page 409 (1988)). These tests are read in a certain scale, for example, skin tests from 0 to 4+. Based on test results, the initial dose is determined. Generally, desensitization is started at a concentration of 1:10,000 w/v, but if the patient is extremely sensitive either by clinical history and/or skin tests result of 4+, it may be appropriate to start at a concentration of 1:100,000. This is a clinical decision which is specific for each and can be readily made by one of ordinary skill in the art, i.e., a physician.

The present invention is directed to an implantable, slow-release, self-absorbing pharmaceutical composition containing one or more active agents in combination with a biologically-compatible, self-absorbing matrix.

The present invention is further directed to a slow-release, self-absorbing, allergy desensitization composition containing one or more allergens in combination with a biologically-compatible, self-absorbing matrix.

The present invention is also directed to a method of desensitizing from one or more allergens, a patient suffering from allergies caused by said one or more allergens by administering to the patient a slow-release, self-absorbing, allergy desensitization composition, the composition containing one or more allergens in combination with a biologically-compatible, self-absorbing matrix, in an amount effective to desensitize the patient to the allergens.

The present invention is directed to a method for desensitizing from one or more allergens, a patient suffering from allergies by subcutaneously implanting in the patient a slow-release, self-absorbing allergy desensitization composition, the composition containing one or more allergens in combination with a self-absorbing, biologically-compatible matrix, in an amount effective to desensitize said patient to said allergens.

The present invention is also directed to a method for desensitizing from one or more allergens, a patient suffering from allergies by serially implanting over time, at least one dosage unit of a slow-release, self-absorbing allergy desensitization composition, the composition containing one or more allergens in combination with a self-absorbing, biologically-compatible matrix, where each dosage unit of the series increases in concentration from the prior dosage unit.

The present invention is also directed to a method for desensitizing an allergy patient from one or more allergens by a series of one or more dosage units of the present slow-release, self-absorbing allergy desensitization composition over time serially subcutaneously implanting in the patient, where a first dosage unit has a lowest concentration and each subsequent dosage unit has a higher concentration than the previous dosage unit in the series and where each dosage unit is implanted in the patient prior to the complete absorption of the previous dosage unit.

The present invention is further directed to an implantation device for subcutaneously implanting the present slow-release, self-absorbing, pharmaceutical composition in a patient, comprising a hollow cylindrical member having an inlet and an outlet, a hollow stylet having a sharp needle-like end and a blunt end, the stylet being slidable disposed within the cylindrical member such that the needle-like end is in slidable connection with the outlet of the hollow cylindrical member, and the blunt end extends beyond the hollow cylindrical member at the inlet end; and a pair of wings connected to a set of prongs present on the inlet of the hollow cylindrical member, where the hollow cylindrical member defines a hollow cylindrical unit.

The present invention is directed to an allergy-desensitization kit for use in desensitizing an allergy patient to one or more allergens, containing a series of one or more vials, each vial containing a single dosage unit of the present slow-release, self-absorbing allergy desensitization composition at a particular concentration, where a first vial contains a dosage unit having a first lowest concentration, while subsequent vials each contain a single dosage unit having a serially higher concentration than the previous vial in the series; packaged together with a device for subcutaneously implanting the present allergy desensitization composition in a patient, where the composition comprises one or more allergens in combination with a slow-release, self-absorbing, biologically-compatible matrix.

The present invention is directed toward an allergy desensitization kit for desensitizing an allergy patient to one or more allergens, containing a series of sterile disposable subcutaneous implantation devices, each device being pre-loaded with a sterile single dosage unit of the present slow-release, self-absorbing allergy desensitization composition containing one or more allergens in combination with a self-absorbing, biologically-compatible matrix, where each dosage unit contained in a separate device, increases in concentration from a first device having a first lowest concentration.

The present invention is directed to an implantation device for subcutaneously implanting the present allergy desensitization composition in a single-use disposable, sterile implantation device, where the device has a surgical steel stylet, and a polymeric hollow cylindrical member and a surgical steel pair of wings.

The present invention also is directed to a multi-use, implantation device for subcutaneously implanting the present allergy desensitization composition in a patient, where the device is produced from surgical steel.

The present invention is directed to a single-use, disposable implantation device for subcutaneously implanting the present allergy desensitization composition in a patient, where the device is produced from a polymeric material.

DESCRIPTION OF THE FIGURES

FIG. 1. FIG. 1 illustrates a cross-sectional view of the present subcutaneous implantation device, (1) represents the hollow cylindrical member having an outlet end; (2) an inlet end; (3) the inlet end (3) may be held or pulled by a set of prongs (4); (5) represents the hollow stylet having a needle-like end (6) and a blunt end (7) and comprises a set of wings (8) with prongs (4); and (1) represents the present slow-release, self-absorbing, pharmaceutical composition pre-loaded on said device.

FIG. 2. FIG. 2 represents a dimensional view of the present device.

DETAILED DESCRIPTION OF THE INVENTION

I. Definitions

To aid in the understanding of the specification and claims, including the scope to be given such terms, the following definitions are provided.

Active Agent.

By the term "active agent" is intended any substance or medication beneficial to a patient for example, a human, and where the substance or medication is amenable to administration in the form of a slow-release, self-absorbing composition, suitable active agents include, for example, one or more allergens, one or more antibiotics, one or more vitamins, one or more hormones, and any combination thereof. Allergens include, for example, oak pollen, meadow grass fescue pollen, ragweed pollen, house dust mite (Dermatophagoides Pteronyssinus), Dog dander allergen, etc. Enclosed is a list of allergens present in the area, either seasonally, like pollens, or perennially such as house dust or house dust mites or molds.

Administration.

By the terms "administration" is intended for the purposes of the present invention the implantation of the present slow-release, self-absorbing, pharmaceutical composition into a patient. Preferably, the present pharmaceutical composition is implanted in the subcutaneous tissue of a patient at a site selected by one of ordinary skill in the art based upon an understanding of the particular disorder being treated and the particular active agents. For example, allergy desensitization compositions are preferably implanted in the internal aspect of the arm or thigh could be a site for injection, in the subcutaneous area. In addition, the dosage, dosage frequency, and length of course of treatment, can be readily determined and optimized by one of ordinary skill in the art for a particular disorder.

Allergen.

By the term "allergen" is intended for the purposes of the present invention, an antigen.

Allergoid.

By the term "allergoid" is intended one or more chemically modified allergens that give rise to antibody of the IgG class but not the IgE class thereby reducing allergic symptoms.

Allergy.

By the term "allergy" is intended for the purposes of the present invention an incident of altered immune reactivity caused by an allergen (i.e., hypersensitivity). Also, by the term "allergy" is intended for the purposes of the present invention an acquired or induced sensitivity, the immunologic state induced in a susceptible subject by an antigen (allergen) characterized by a marked change in the subject's reactivity, on initial contact with the antigen no immunologic reaction occurs, but after a latent period of several days to two weeks or so, the subject may become sensitive, even to antigen that persists from the initial inoculation (as in serum sickness), thereafter a specific antigen invokes a reaction within minutes or hours, a failure which depends upon quantitative relationships and route or entrance.

Amount Fffective To Desensitize.

By the term "amount effective to desensitize" is intended for the purposes of the present invention, that amount of the present slow-release, self-absorbing biologically-compatible allergy desensitization composition effective to reduce or ameliorate a patient's sensitivity to one or more allergens.

Biologically-Compatible.

By the terms "biologically-compatible" is intended for the purposes of this invention, any material which does not provoke an adverse response in a patient. For example, a suitable biologically-compatible material when introduced into a patient does not itself provoke a significant antibody response. Also, by the terminology "biologically-compatible" for the purposes of the present invention is intended the ability of the present self-absorbing matrix to exist together in the patient without nullification of, or deleterious effects on, the function of either the matrix or the patient such that no reaction is caused.

Desensitize.

By the term "desensitize" is intended for the purposes of this invention to deallergize, that is reduce or remove any form of sensitivity. Likewise, by the term "desensitization" is intended for the purposes of the present invention the reduction or abolition of allergic sensitivity or reactions to a specific allergen. Both "heterologous desensitization" the stimulation by one agonist which leads to a broad pattern of unresponsiveness to further stimulation by a variety of other agonists and "homologous desensifization", the loss of sensitivity only to a class of agonist used to desensitize the tissue, are intended.

Disorder.

By the terms "disorder" is intended for the purposes of the present invention any condition amenable to treatment with an active agent in the form of a slow-release, self-absorbing matrix. Such disorders include allergic disorders, vitamin deficiencies and infections. The physician would determine if an allergic condition is amenable to treatment with the "slow release, self-absorbing matrix" by evaluating the clinical history of the patient, together with allergy tests that would indicate what allergies the patient has; and putting together the clinical history and the results of allergy tests, a treatment method is prescribed.

Dosage Unit.

By the term "dosage unit" is intended for the purposes of the present invention that physical unit which is subcutaneously implanted in a patient, which dosage unit contains one or more active agents in one or more self-absorbing, biologically-compatible matrixes where the active agents are at a predetermined concentration.

Multiple Dosage Unit.

By the term "multiple dosage unit" is intended for the purposes of the present invention that physical unit which is subcutaneously implanted in a patient, which dosage unit contains one or more active agents in one or more self-absorbing, biologically-compatible matrixes, where the active agents are present in increasing concentrations from an outermost layer having a lowest concentration to an inner most layer having a highest concentration, where the layers are not distinct, but are gradual.

Hyposensitization.

By the term "hyposensitization" is intended the act of reducing sensitivity of a patient, in which the response to an allergen is delayed or lessened in degree.

Implant.

By the term "implant" is intended for the purposes of the present invention reactive grafting or inserting a material into tissues.

Patient/Individual.

By the terms "patient" or "individual" is intended for the purposes of the present invention, animals including humans and mammals, who suffer from one or more disorders.

Self-Absorbing.

By the term "self-absorbing" is intended for the purposes of the present invention the property of a biologically-compatible matrix to be absorbed by a patient's tissue. Suitable self-absorbing matrices include the following materials, for example: polydioxanone, for example, including those disclosed in U.S. Pat. No. 5,019,094, issued May 28, 1991 to Bezwada et al., those disclosed in U.S. Pat. No. 4,122,129 dated Oct. 24, 1978, to Casey et al., and U.S. Pat. No. 5,403,347, issued Apr. 4, 1995 to Roby et al, polyglycolic acid and polyglactic acid.

Sensitization.

By the term "sensitization" it intended for the purpose of this invention the induction of acquired sensitivity or of allergy. Likewise, by the term "sensitize" is intended for the purposes of this invention to render sensitive or to induce acquired sensitivity.

Serial Implantation.

By the term "serial implantation" is intended for the purposes of the present invention, the act of implanting a series of dosage units of the present pharmaceutical composition subcutaneously in a patient where the series increases in concentration of the active agent and where a lowest concentration dosage unit of the series is implanted, and prior to or less than two weeks after, the complete release of the active agent from the matrix of the dosage unit (complete absorption of the dosage unit). A subsequent member of the series having a higher concentration of active agent is then subcutaneously implanted in the patient. One of ordinary skill in the art can readily determine appropriate concentrations of active agent in a particular dosage unit as well as a suitable schedule for serially implanting each dosage unit.

Slow-Release.

By the term "slow-release" is intended for the purposes of the present invention, the gradual release of an active agent from a matrix into a patients tissue.

Subcutaneous.

By the term "subcutaneous" is intended for the purposes of this invention, beneath the skin. Subcutaneous is also called hypodermatic, hypodermic, subdermic, subintegumental, and subtegumental.

Subcutaneous Implant.

By the term "subcutaneous implant" is intended for the purposes of the present invention, material which has been implanted (inserted or grafted) beneath the skin of a patient.

II. Production of Pharmaceutical Compositions

The present allergy desensitization compositions and the present pharmaceutical compositions, both of which are biologically-compatible, self-absorbing and slow-release are administered in the form of a dosage unit. A dosage unit may be formulated to allow the active agent to be continuously absorbed or in a bolus form where the dosage unit is produced having alternate layers of active agent and matrix, such that the active agent is released, followed by no presentation of the active agent and thereafter, for example, followed by presentation of the active agent. The maintenance matrix would contain 60 mg of allergy extract, mixed homogeneously with the matrix material and there would be more matrix material to provide for a longer period of absorption at the same rate of absorption. The initial matrix would, for example, contain 10 mg of allergen and less matrix material, homogeneously distributed.

The allergy desensitizing matrices are produced under sterile conditions by mixing the dried allergy extract with the self-absorbing material (for example, polydioxanone (PDS), polyglycolic acid (Dexon $(CH_3)_2NC_6H_4NNSO_3Na$ para-dimethylaminobenzediazone sodium sulfonate, melts with decomposition at above 200° C., soluble in $H_2O$), or other self-absorbing material such as polyglactic acid (vicryl)). These allergen and self-absorbing materials are mixed homogeneously in the liquid form and then allowed to dry, forming the dosage unit. The dosage unit can be of any physical shape which shape allows the implantation into the patient by, for example, injection. Suitable physical shapes include, for example, a solid cylinder or an angiocath type hollow sleeve.

Suitable matrix materials and methods for making them include those disclosed, for example, in: U.S. Pat. Nos.: 3,468,853; 3,297,033; 3,435,008; 2,683,136; 3,457,280; 3,442,871; and 3,597,450, hereby incorporated herein in their entirety.

Once matrix materials and the active agents are selected, the matrix materials are melted and slowly cooled. Prior to solidification of the homogeneously melted material or materials, the active agent is homogeneously mixed therewith and thereafter cooled to produce the present composition.

Traditionally, allergy injections are started at a low concentration and volume and given every week or twice a week progressively increasing the volume, and when 0.5 ml is reached, a new vial of higher concentration is started and the process is continued until maintenance is reached.

In the present system the dry weight equivalent of all the injections in each concentration is mixed with one or more self-absorbing materials and implanted by a single injection as opposed to approximately 10 sessions that it would take using the traditional method.

There are 0.05 mg of dry allergy extract in 0.5 ml of 1:10,000 w/v allergy extract. The total volume injected in a series of desensitization injections at this concentration would be 0.275 mg.

Different types of self-absorbing materials are absorbed at varying rates. For example, a self-absorbing material in the form of a suture at a regular suture thickness is totally reabsorbed by hydrolysis in 60–90 days in the case of polyglycolic acid (Dexon), in 60 days for polyglactic acid, and even longer for polydioxanone (PDS). Therefore, a desired rate of absorption is achieved by varying the total mass of absorbable material, leaving the surface area stable or unchanged. An initial dosage unit could contain, for example, 0.275 mg of dried allergy extract homogeneously mixed with one or more self-absorbing materials in liquid form, to produce the first matrix dosage unit to be used in the desensitization process.

Thereafter, prior to the complete absorption of the first matrix, the second matrix is implanted. The second matrix, for example, is equivalent to 1:1000 w/v since there are 2.75 mg of dried extract in 2.75 ml of 1:1000. The dried weight of 2.75 mg is then mixed with one or more self-absorbing materials to form the second matrix dosage unit.

The third dosage unit, for example, is equivalent to 1:100 w/v, and contains 27.5 mg of dried extract. The fourth dosage unit, for example, is equivalent to 1:50 w/v and contains 55 mg of dried extract.

After implantation of the fourth dosage unit has been well tolerated, but not completely reabsorbed, a maintenance matrix, for example, containing six (6) times the dry allergen (for example, 330 mg of dried extract) and six (6) times the mass of self-absorbing material or a different combination of self-absorbing materials including, for example, PDS, to allow for large absorption times, would be implanted. This maintenance dosage unit is thereafter implanted at approximately six month intervals. The total mass of self absorbing material would vary, depending on which material is used, for example, if polyglycolic acid (Dexon) is used and it is absorbed in 90 days, then only twice the mass would be implanted to be absorbed in six (6) months.

Desensitization may also be achieved in cases where a patient cannot return to the doctor's office at regular intervals.

In those cases the multiple dosage unit consists of concentric layers of matrix-allergen with the outermost layer having a lowest concentration of allergen and each subsequent inner layer having an increase in concentration of allergen with the innermost layer having a highest concentration of allergen. The concentration pattern may be as discussed above (in reference to a dosage unit having a single allergen concentration) except where a single dosage unit has those concentrations in gradual layers with the innermost layer having a highest concentration of allergen. The layers are not distinct, they rather gradually increase in concentration towards the middle, therefore minimizing the risk of a new bolus of a more concentrated allergen being absorbed when the patient is not at the doctor's office, in a controlled environment.

III. Therapeutic Applications

A. Allergy Desensitization Compositions

Prior to treatment with the present biologically-compatible, slow-release, self-absorbing, allergy desensitization compositions, the specific allergen or allergens to which a patient is sensitized must be determined for example, by taking a careful patient history and by skin tests. Thereafter, depending upon the degree of sensitivity of the patient to a particular antigen and the rate of absorption of the matrix by a patient, one of ordinary skill in the art such as an allergist, can readily determine the concentration of the allergen or allergens for inclusion in the matrix of a first dosage unit necessary to hyposensitize the patient.

The subcutaneous implantation of the present allergy desensitization composition stimulates the formation of an IgG blocking antibody which remains in the circulation of tissues. Upon exposure to antigen, these antibodies react with the antigen forming a complex which is then removed by the reticuloendothelial system. Thus, since the antigen cannot reach the IgE on the target cells, the allergic reaction does not take place. Secondly, IgE immune tolerance may be induced, where IgE antibody production is suppressed by continued immunotherapy (slow-release of the present allergen from the present composition). If no IgE is produced, then continued sensitization of the mast cells does not occur. Lastly, the subcutaneous implantation of the present allergy desensitization composition may result in target cell desensitization. For example, a child with both Ragweed and Alternaria allergies, when treated with Ragweed alone, exhibits a decrease in the leukocyte histamine release with both Ragweed and Alternaria.

During initial therapy, circulating IgE antibody increases slightly and then gradually falls below pretreatment levels over a period of several years. Blocking antibody, which is IgG with specificity for the particular allergen that binds circulating allergen without initiating a type I reaction, appears in the serum of most treated patients. The normal post seasonal rise in IgE antibody to pollens is diminished indicating that treatment induces a form of partial immunologic tolerance.

Suitable allergens for use in the present allergy desensitization composition include any material which gives rise to allergic sensitization in a patient. Most natural allergens have a molecular weight in the rate of 10 to 70,000 daltons. The present allergens can be treated with mild formalin and/or glutaraldehyde to form allergoids. These allergoids can then be used as the allergen in the present allergy desensitization composition. Allergoids reduce the allergenicity (IgE formation) without effecting the antigenicity (IgG blocking antibody formation). Such polymerized pollen antigens greatly enhance IgG blocking antibody production, with little change in IgE antibodies and good clinical improvement.

Suitable allergens for use in the present allergy desensitization composition include allergens and allergens treated with mild formalin and/or glutaraldehyde or the like to form allergoids. Such allergens can include for example, venom, pollen extract, mold, food, and polysaccharides. Examples of venom include bee venom allergen, phospholipase A. Pollens include Ragweed pollen 5.

In atopic allergic disease IgE antibodies fixed to mast cells react with antigen, triggering the release of histamine and the activation of slow-reacting substance (SRS-A) and eosinophil chemotactic factors (ECF-A). This is the mechanism responsible for atopy, anaphylaxis, urticaria and angioedema. The most common form of allergic atopic disease is allergic rhinitis usually caused by seasonal pollen allergy. Allergens which can cause atopic disease include pollens, mold, house dust, animal danders, or food. Fungal spores, animal danders and certain airborne particles in the home are the most common inhalant allergens. Within each geographical location, the common allergenic trees, grasses and weeds pollinate each year during a specific and predictable season. For example, in the midwestern United States of America the important allergenic trees, maple, elm, oak and birch pollinate for six to eight weeks beginning with the Spring thaw; grass pollen appears principally during June and July, and the weeds pollinate from the middle of August until the first frost. Pollinating seasons in the far West are long and overlapping.

Spores of fungi in the soil and air pollinating vegetation are sources of aero allergens and are found in air samples throughout the year. Such allergens include spores of Alternaria, Hormodendrum, Helminthosporium, Aspergillus, Pullularia, Mucor, Rhizopus, and Penicillium. Other allergens include the spores of Rusts and Smuts that infect certain crops and grasses. Also, insect debris has been identified as a cause of allergic symptoms.

The most common indoor allergen is the house dust mite, *Dermatophagoides Farinae* or *Dermatophagoides Pteronyssinus*. Feathers as well as dander or excretion (saliva) from certain household pets including for example, cats, dogs, hamsters, guinea pigs or from horses, farm stock, or zoo animals can also cause allergies. Further, the chronic inhalation of, for example, wheat flour can cause allergic rhinitis or asthma.

Allergenic tree pollens in the south eastern coastal plain include: red cedar, hackberry, elm, pecan, hickory, willow, poplar, ash, birch, sweet gum, maples, sycamore, mulberry, oak, and walnut.

Allergenic plant pollens and mold spores in the San Francisco Bay Area include the following: (i) Trees and Shrubs: including Acacia, Alder, Ash, Birch, Box Elder, Cottonwood, Cyprus, Elm, Juniper, Laroak, Mulberry, Olive, Privet, Sycamore, and Walnut; (ii) Weeds: including Beach Sand Bur, Cocklebur, English Plantain, Lambs Quarters, Mugwart, Pickleweed, Pigweed, Ragweed, False Ragweed, Western Russian Thistle, Sheep Sorrel, and Wingscale; (iii) Grasses: including Bermuda, Bluegrass, Brome, Orchard, Perennial Rye, Sweet Vernal, Velvet, and Wildoat; and (iv) Fungi: including Alternaria, Aspergillus, Cephalothecium, Fusarium, Helminthosporium, Hormodendrum, Mucor, Penicillium, and Rhisopus. Other allergenic pollens from different geographical locations suitable for use in the present allergy desensitization compositions include those disclosed in Sampter, N., Durum O C, *Regional Allergy of the U.S., Canada, Mexico and Cuba*, Thomas (1955) and Ross, A., *Allergy In The World*, University Press of Hawaii (1978). (*Allergy, Principles & Practice*, Middleton, Reed, Ellis, Adkinson, Yunginger, 3rd Edition. *Pollen Prevalence in North American Floristic Zones*, pp. 337–342 (1988). This section of the book summarizes the distribution and seasonal prevalence of windborne pollens in the United States and the world. See also: *Allergy Plants* by Mary Jelks, M.D., Worldwide Printing, Tampa, Fla.; *Sampling and Identifying Allergenic Pollens and Molds, An Illustrated Manual for Physicians and Lab Technicians*, E. Grant Smith, Blewstone Press, San Antonio, Tex. (1984).

The present immunotherapy (hyposensitization) using the present methods and allergy desensitization compositions effectively reduces allergy symptoms, for example, symptoms of allergic rhinitis in patients with seasonal pollen allergy and also in patients with mold or dust allergy.

Clinical improvement during immunotherapy correlates better with blocking antibody response than with other immunologic changes, but a combination of several mechanisms might be required for optimal results.

The present allergy desensitization compositions and methods can also be used for treating hypersensitivity due to stinging insects. Suitable allergens in this case, for inclusion in the present compositions include hymenoptera venoms, venoms from the honey bee, yellow jacket, wasps, and hornets.

The venom of these insects contain protein allergens in addition to the pharmacologically active chemicals responsible for the usual local inflammation. In the honey bee family (Aphidae) venom, the major allergen is phospholipase $A_{21}$ and the minor allergens are hyaluronidase and melittin. In vespids (family vespidae), which includes hornets, yellow jackets, and wasps, the venom allergens are: yellow jacket: phospholipase A B, hyaluronidase, kinin, antigen 5; hornet: most of these plus a kinin labeled "hornet kinin", antigen 5; Wasp: phosphoidase A B, hyaluronidase, antigen 5. Kinins are components of venom not identified as allergens.

The sting of a single insect is sufficient to produce a severe, even fatal anaphylactic reaction in sensitive patients. Sensitization occurs from prior stings, and if patients are allergic to a common or cross reacting antigen they may have an anaphylactic reaction should they be stung by any species of hymenoptera insect. Accordingly, allergens for use in the present compositions include the venom of honey bees, wasps, hornets, yellow jackets, and fire ants.

Prior to the onset of immunotherapy, the practitioner must determine the particular allergen or allergens responsible for the hypersensitivity in the patient. Thereafter, one of ordinary skill in the art, can readily determine the correct dosage level for the particular patient, including the initial dosage, subsequent increasing dosages, and final maintenance dose levels.

Once an initial dose is determined, treatment is begun at a dosage low enough to avoid any local or systemic reactions. For example, the present allergy desensitization composition containing a particular allergy extract or extracts, (aqueous/phenol weight/volume) in the present self-absorbing, biologically-compatible matrix can be subcutaneously implanted in the patient at for example a concentration of about 1 to 10,000 w/vol. matrix. Subsequent dosage units are implanted at increasing dosages at approximately two weeks to three month intervals, preferably one month intervals, until the highest dose the patient can tolerate without experiencing a local or systemic reaction, is reached. This is the maintenance dose. At this dose swelling up to three or four millimeters in diameter lasting less than 24 hours and accompanied by erythema and itching is to be expected. The maintenance dose is then continued at less frequent intervals, usually about every two to ten months, preferably every four to eight months, and more preferably every six months. The duration of time between the implantation of each dosage unit can be readily determined by one or ordinary skill in the art and depends upon the sensitivity of the patient to the allergen and the rate of absorption of the allergy desensitization composition by the patient's tissues. It should be noted that if treatment is begun during the pollen season, the starting dose must be quite low to avoid reaction.

Alternatively, immunotherapy can begin three to six months before the anticipated start of the pollen season, and the treatment is stopped just before the seasons begins. This procedure is repeated each year; however, this is a more cumbersome method to use in patients with multiple seasonal allergies.

The present invention includes allergy desensitization compositions containing one or more allergens either in the form of an allergen extract or chemically modified or polymerized allergen to render the allergen molecule less allergenic while retaining or enhancing its immunogenicity for treatment.

B. Other Biologically-Compatible, Slow-Release, Self-Absorbing Pharmaceutical Compositions The present pharmaceutical compositions can be subcutaneously implanted in a patient to effect the slow-release of a desired active agent. Suitable active agents include for example, heterologous proteins such as hormones or enzymes, polysaccharides, and therapeutic agents including for example antibiotics and vitamins including the following:

(i) antibiotics such as third generation cephalosporins, penicillins, erythromycins, aminoglycosides;

(ii) antidotes such as anticholinesterases, Digoxin;

(iii) anti-inflammatory agents such as steroids;

(iv) contraceptives, parenteral;

(v) vasodilators, cerebral such as papaverine hydrochloride used under doctor's orders for conditions such as vascular spasm associated with acute myocardial infarction (coronary occlusion), angina pectoris, peripheral and pulmonary embolism, peripheral vascular disease in which there is vasospastic element, or certain cerebral angiospastic states; and visceral spasm as in ureteral, biliary or gastrointestinal colic;

(vi) vasodilators, coronary such as nitroglycerin for treatment of angina pectoris;

(vii) doxapram hydrochloride a respiratory stimulant used in postanesthesia respiratory depression;

(viii) somatropin (recombinant DNA origin) having an amino acid sequence indentical to human growth hormone, used to stimulate linear growth in children who lack adequate normal endogenous growth hormone;

(ix) hormones;

(x) anticoagulants such as heparin;

(xi) antihypertensives; and (xii) anticonvulsants (seizure disorders).

One of ordinary skill in the art can readily determine, based on the patient's sensitivity to a particular active agent and the rate of absorption of the pharmaceutical composition by the patient's tissues, the appropriate dosage level, intervals between the implantation of a particular dosage unit, and the length of course of treatment.

Although the invention has been described with reference to particular means, materials and embodiments, it is to be understood that the invention is not limited to the particulars disclosed and extends to all equivalents within the scope of the claims. All references cited herein are hereby incorporated by reference in their entirety.

What is claimed:

1. A slow-release, self-absorbing pharmaceutical composition comprising one or more active agents in combination with a biologically-compatible, self-absorbing matrix material, said one or more active agents mixed homogeneously with said biologically-compatible, self-absorbing matrix material to form a biologically-compatible, self-absorbing dry solid matrix, said matrix being shaped to be one selected from the group consisting of a solid cylinder and a hollow sleeve, and otherwise suitably configured for subcutaneously implanting with an injecting device.

2. A slow-release, self-absorbing allergy desensitization composition comprising one or more allergens in combination with a biologically-compatible, self-absorbing matrix material, said one or more active agents mixed homogeneously with said biologically-compatible, self-absorbing matrix material to form a biologically-compatible, self-absorbing dry solid matrix, said matrix being shaped to be one selected from the group consisting of a solid cylinder and a hollow sleeve, and otherwise being suitably configured for subcutaneous implanting with an infecting device.

3. The slow-release, self-absorbing pharmaceutical composition of claim 1, wherein said biologically-compatible, self-absorbing matrix comprises one or more self-absorbing biologically-compatible materials.

4. The slow-release, self-absorbing pharmaceutical composition of claim 3, wherein said one or more self-absorbing, biologically-compatible materials are selected from the group consisting of: polydioxanone, polyglycolic acid and polyglactic acid.

5. The slow-release, self-absorbing allergy desensitization composition of claim 2, wherein said biologically-compatible, self-absorbing matrix comprises one or more self-absorbing biologically-compatible materials.

6. The slow-release, self-absorbing allergy desensitization composition of claim 5, wherein said one or more self-absorbing, biologically-compatible, materials are selected from the group consisting of: polydioxanone, polyglycolic acid and polyglactic acid.

7. The allergy-desensitization kit of any one of claims 3 or 4, wherein said biologically-compatible matrix comprises one or more self-absorbing, biologically-compatible materials.

8. The allergy-desensitization kit of claim 7, wherein said one or more self-absorbing, biologically-compatible materials are selected from the group consisting of: polydioxanone, polyglycolic acid and polyglactic acid.

9. The pharmaceutical composition of claim 1, wherein said pharmaceutical composition comprises a single dosage unit.

10. The pharmaceutical composition of claim 1, wherein said pharmaceutical composition comprises a multiple dosage unit.

11. The pharmaceutical composition of claim 9, wherein said pharmaceutical composition comprises a single dosage unit.

12. The pharmaceutical composition of claim 10, wherein said pharmaceutical composition comprises a single dosage unit.

* * * * *